(12) United States Patent
Yang et al.

(10) Patent No.: US 11,633,132 B2
(45) Date of Patent: Apr. 25, 2023

(54) APPARATUS AND METHOD FOR ANALYZING IN VIVO COMPONENT AND IMPEDANCE MEASURING APPARATUS

(71) Applicants: SAMSUNG ELECTRONICS CO., LTD., Suwon-si (KR); GWANGJU INSTITUTE OF SCIENCE AND TECHNOLOGY, Gwangju (KR)

(72) Inventors: Sung Yang, Gwangju (KR); Kun Sun Eom, Yongin-si (KR); Myoung Hoon Jung, Bucheon-si (KR); Byung Jun Kim, Gwangju (KR); Alexander Zhbanov, Gwangju (KR); Seung Yeob Lee, Gwangju (KR); Ye Sung Lee, Gwangju (KR)

(73) Assignees: SAMSUNG ELECTRONICS CO., LTD., Suwon-si (KR); GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 109 days.

(21) Appl. No.: 16/743,119

(22) Filed: Jan. 15, 2020

(65) Prior Publication Data

US 2020/0323468 A1 Oct. 15, 2020

(30) Foreign Application Priority Data

Apr. 12, 2019 (KR) .......... 10-2019-0043265

(51) Int. Cl.
*A61B 5/1477* (2006.01)
*A61B 5/00* (2006.01)
(Continued)

(52) U.S. Cl.
CPC ........ *A61B 5/1477* (2013.01); *A61B 5/14532* (2013.01); *A61B 5/14546* (2013.01);
(Continued)

(58) Field of Classification Search
CPC .......... G16H 50/50; A61B 5/14546; A61B 5/14532; A61B 5/0537
See application file for complete search history.

(56) References Cited

U.S. PATENT DOCUMENTS

2007/0074977 A1\* 4/2007 Guo .................. A61B 5/14532
205/792
2008/0057526 A1 3/2008 Caduff et al.
(Continued)

FOREIGN PATENT DOCUMENTS

KR 10-2017-0135368 A 12/2017
KR 10-2018-0036681 A 4/2018
WO 2010045247 A1 4/2010

OTHER PUBLICATIONS

Appendix 1 to the Oct. 2019 Update: Subject Matter Eligibility; Life Sciences & Data Processing Examples, Example 46 (Year: 2019).\*

*Primary Examiner* — Christian Jang
(74) *Attorney, Agent, or Firm* — Sughrue Mion, PLLC

(57) ABSTRACT

An apparatus for analyzing an in vivo component is provided. The apparatus for analyzing an in vivo component may include an impedance sensor including a first electrode and a second electrode configured to contact a fluid channel of a fluid to be analyzed. The apparatus may include an impedance measurement device configured to apply a current to the first electrode and the second electrode, measure a voltage between the first electrode and the second electrode based on applying the current, and measure an impedance of the fluid based on the measured voltage. The apparatus may include a processor configured to model the measured impedance using an equivalent circuit; and analyze the in vivo component based on modeling the measured impedance using the equivalent circuit.

9 Claims, 9 Drawing Sheets

(51) Int. Cl.
    *A61B 5/145*     (2006.01)
    *G01N 27/02*     (2006.01)
    *G16H 50/20*     (2018.01)
    *G16H 50/50*     (2018.01)
    *G16B 5/00*     (2019.01)

(52) U.S. Cl.
    CPC ............ *A61B 5/681* (2013.01); *A61B 5/7214* (2013.01); *G01N 27/02* (2013.01); *G16B 5/00* (2019.02); *G16H 50/20* (2018.01); *G16H 50/50* (2018.01)

(56) References Cited

U.S. PATENT DOCUMENTS

| | | | |
|---|---|---|---|
| 2008/0214910 A1* | 9/2008 | Buck | A61B 5/1495 600/310 |
| 2009/0312615 A1 | 12/2009 | Caduff et al. | |
| 2010/0075353 A1* | 3/2010 | Heaton | G16H 20/60 435/14 |
| 2010/0099960 A1 | 4/2010 | Caduff et al. | |
| 2010/0130883 A1 | 5/2010 | Carpenter et al. | |
| 2010/0234701 A1 | 9/2010 | Cho et al. | |
| 2011/0230741 A1 | 9/2011 | Liang et al. | |
| 2013/0211204 A1 | 8/2013 | Caduff et al. | |
| 2013/0211280 A1* | 8/2013 | Gregory | A61B 5/0536 600/547 |
| 2016/0320329 A1 | 11/2016 | Buck, Jr. et al. | |
| 2017/0164878 A1 | 6/2017 | Connor | |
| 2017/0181677 A1 | 6/2017 | Varsavsky et al. | |
| 2018/0116570 A1 | 5/2018 | Simpson et al. | |
| 2018/0223324 A1 | 8/2018 | Tonks | |

\* cited by examiner

APPARATUS AND METHOD FOR ANALYZING IN VIVO COMPONENT AND IMPEDANCE MEASURING APPARATUS

CROSS-REFERENCE TO RELATED APPLICATION(S)

This application claims priority from Korean Patent Application No. 10-2019-0043265, filed on Apr. 12, 2019, in the Korean Intellectual Property Office, the disclosure of which is incorporated by reference herein in its entirety.

BACKGROUND

1. Field

Example embodiments of the present disclosure relate to an apparatus and method for analyzing in vivo components using bio-impedance.

2. Description of Related Art

Various medical devices are being developed for diagnosis of health conditions of patients. The importance of medical devices for measuring electric bio-signals of patients is emphasized in the process of medical examinations to improve patient convenience and to provide prompt medical examination results. Particularly, bio-impedance may be used to monitor physical or emotional conditions of the body, and various studies are being conducted to manufacture small devices for measuring such bio-impedance, and to provide methods of rapidly and accurately measuring the bio-impedance.

SUMMARY

In accordance with an aspect of the disclosure, an apparatus for analyzing an in vivo component may include an impedance sensor including a first electrode and a second electrode configured to contact a fluid channel of a fluid to be analyzed. The apparatus may include an impedance measurement device configured to apply a current to the first electrode and the second electrode, measure a voltage between the first electrode and the second electrode based on applying the current, and measure an impedance of the fluid based on the measured voltage. The apparatus may include a processor configured to model the measured impedance using an equivalent circuit; and analyze the in vivo component based on modeling the measured impedance using the equivalent circuit.

The impedance measurement device may measure the impedance at a plurality of frequencies within a predetermined range.

The equivalent circuit may include a plurality of resistors and a plurality of capacitors.

The processor may reduce an effect of noise, including at least one of a parasitic component and a polarization effect of the impedance sensor, from the measured impedance.

The processor may extract one or more parameters, related to properties of the fluid to be analyzed, based on modeling the equivalent circuit.

The parameters may include at least one of plasma resistance, cytoplasm resistance, plasma capacitance, and constant phase element (CPE) of a cell membrane.

The processor may obtain a parameter variation by normalizing the extracted one or more parameters using a parameter at a reference time.

The reference time may correspond to a fasting interval.

The processor may obtain an estimated in vivo component value, including at least one of blood glucose, cholesterol, triglyceride, protein, and uric acid, by applying an in vivo component estimation model to the parameter variation.

The fluid channel of the fluid to be analyzed may comprise a blood vessel portion of an object.

The fluid channel of the fluid to be analyzed may include an inlet configured to introduce the fluid to be analyzed, a storage configured to store the fluid introduced via the inlet, and an outlet configured to discharge the fluid stored in the storage.

The impedance sensor may include a fluid property adjustment device configured to adjust at least one of a temperature and a flow property of the fluid to be analyzed.

The first electrode may contact a first side of the channel, the second electrode is may contact a second side of the channel, and the first electrode and the second electrode are disposed to face each other.

In accordance with an aspect of the disclosure, a method of analyzing an in vivo component may include applying a current to a first electrode and a second electrode of an impedance sensor, measuring a voltage between the first electrode and the second electrode based on applying the current, measuring an impedance of a fluid to be analyzed based on the measured voltage, modeling the measured impedance using an equivalent circuit, and analyzing the in vivo component based on modeling the measured impedance using the equivalent circuit.

The modeling of the measured impedance using the equivalent circuit may include reducing an effect of noise, including at least one of a parasitic component and a polarization effect of the impedance sensor, from the measured impedance.

The modeling of the measured impedance using the equivalent circuit may include extracting one or more parameters, related to properties of the fluid to be analyzed, based on modeling the equivalent circuit.

The analyzing of the in vivo component may include obtaining a parameter variation by normalizing the extracted one or more parameters using a parameter at a reference time.

The analyzing of the in vivo component may include obtaining an estimated in vivo component value, including at least one of blood glucose, cholesterol, triglyceride, protein, and uric acid, by applying an in vivo component analysis model to the parameter variation.

The method may include adjusting at least one of a temperature and a flow property of the fluid to be analyzed.

In accordance with an aspect of the disclosure, an impedance measuring apparatus may include a first electrode configured to contact a first side of a fluid channel of a fluid to be analyzed, a second electrode configured to contact a second side of the fluid channel of the fluid to be analyzed, and that is disposed to face the first electrode, a fluid property adjustment device configured to adjust a property of the fluid to be analyzed, and an impedance measurement device configured to apply a current to the first electrode and the second electrode, measure a voltage between the first electrode and the second electrode based on applying the current, and measure an impedance of the fluid based on the measured voltage.

BRIEF DESCRIPTION OF THE DRAWINGS

The above and/or other aspects will be more apparent from the following description of example embodiments taken in conjunction with the accompanying drawings, in which.

DETAILED DESCRIPTION

Figure 1:
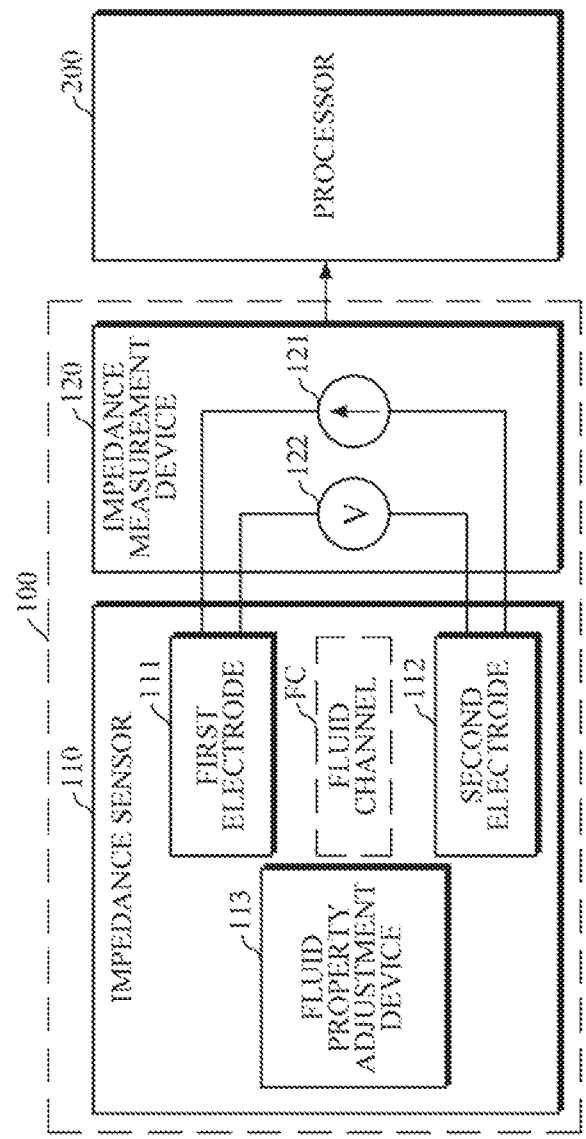
FIG. 1 is a block diagram illustrating an apparatus for analyzing an in vivo component according to an example embodiment.

Details of example embodiments are included in the following detailed description and drawings. Advantages and features of the present disclosure, and a method of achieving the same will be more clearly understood from the following embodiments described in detail with reference to the accompanying drawings. Throughout the drawings and the detailed description, unless otherwise described, the same drawing reference numerals may refer to the same elements, features, and structures. The relative size and depiction of these elements may be exaggerated for clarity, illustration, and convenience.

It should be understood that, although the terms such as "first," "second," etc., may be used herein to describe various elements, these elements might not be limited by these terms. These terms might be used to distinguish one element from another. Any references to the singular form of a term may include the plural form of the term unless expressly stated otherwise. In addition, unless explicitly described to the contrary, expressions such as "comprising" or "including" may imply the inclusion of stated elements, and might not imply the exclusion of any other elements. Also, terms such as "part" or "module," etc., may refer to a that performs at least one function or operation, and that may be implemented in hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

Hereinafter, example embodiments of an apparatus and method for analyzing an in vivo component will be described in detail with reference to the accompanying drawings.

Figure 2A:
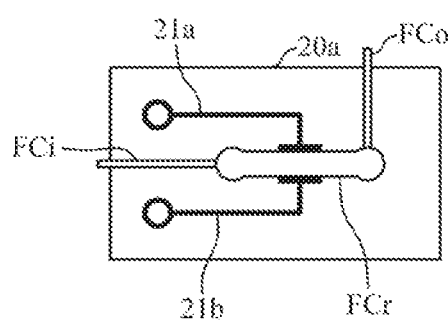
FIGS. 2A and 2B are diagrams illustrating an impedance sensor according to an example embodiment.
Figure 2B:
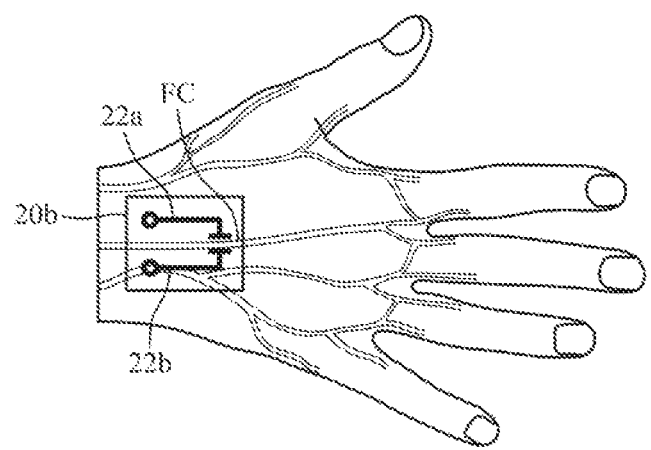

FIG. 1 is a block diagram illustrating an apparatus for analyzing an in vivo component according to an example embodiment. FIGS. 2A and 2B are diagrams illustrating an impedance sensor according to an example embodiment. The apparatus 1 for analyzing an in vivo component according to an example embodiment may be a medical device used in a specialized medical institution, a smart watch configured to be worn on a wrist of a user, a wearable device (e.g., a smart band-type wearable device, a headphone-type wearable device, a headband type-wearable device, and the like), a mobile device such (e.g., a smartphone), a tablet personal computer (PC), and the like.

Referring to FIG. 1, the apparatus 1 for analyzing an in vivo component includes an impedance sensor 110, an impedance measurement device 120, and a processor 200. The impedance sensor 110, the impedance measurement device 120, and the processor 200 of the apparatus 1 for analyzing an in vivo component may be implemented in hardware. However, the apparatus 1 for analyzing an in vivo component is not limited thereto, and some components of the apparatus 1, such as the impedance sensor 110 and the impedance measurement device 120, may be configured as a separate hardware device from the processor 200 to form an impedance measuring apparatus 100. The impedance sensor 110 and the impedance measurement device 120 may be connected to the processor 200 via a wired or wireless connection, and may be configured to communicate with the processor 200 via the wired or wireless connection.

The impedance sensor 110 includes a first electrode 111, a second electrode 112, and a fluid property adjuster 113.

The first electrode 111 and the second electrode 112 may be disposed on a main body substrate, and may be configured to contact a fluid channel FC of a fluid to be analyzed. The first electrode 111 and the second electrode 112 may be disposed to face each other to permit the first electrode 111 to contact a first side of the fluid channel FC of the fluid to be analyzed, and the second electrode 112 to contact a second side of the fluid channel FC. In this case, the fluid to be analyzed may include blood, but is not limited thereto, and may include a sample solution which includes similar physical properties as blood.

The first electrode 111 and the second electrode 112 may be configured to measure impedance using a two-electrode method, a four-electrode method, and the like. When impedance is measured using the two-electrode method, the first electrode 111 and the second electrode 112 each may be provided as separate electrodes. Further, when impedance is measured using the four-electrode method, each of the first electrode 111 and the second electrode 112 may include an input electrode configured to apply a current, and an output electrode configured to measure a voltage applied to the fluid, which is generated by the current applied to the input electrode. The first electrode 111 and the second electrode 112 may include various shapes such as a bar shape, a semi-circular shape, a circular shape, and the like.

Although FIG. 1 illustrates two electrodes 111 and 112, the apparatus 1 is not limited thereto, and may include any number of electrodes. For example, the impedance sensor 110 may include the first electrode 111 and the second electrode 112 which measure impedance using the four-electrode method, and may include a third electrode and a fourth electrode which measure impedance using the two-electrode method.

The fluid property adjuster 113 may adjust the properties of the fluid to be analyzed based on various conditions such as a type of an in vivo component to be analyzed, an analysis purpose, an analysis environment such as ambient temperature, processing performance of the apparatus 1 for analyzing an in vivo component, and the like. The properties of the fluid to be analyzed may include temperature, flow, flow speed, and the like, of the fluid, but are not limited thereto. The fluid property adjuster 113 may include a thermostat, a flow regulator, a flow speed regulator, and the like. For example, when impedance is measured in an in vitro environment, temperature of the fluid in the fluid channel FC may be adjusted to be similar to an internal temperature of the human body.

The impedance measurement device 120 may apply a current to the first electrode 111 and the second electrode 112, and may measure bio-impedance by measuring a voltage applied to the first electrode 111 and the second electrode 112. For example, the impedance measurer 120 may include a current source 121 configured to apply an alternating current, and a voltmeter 122 configured to measure a voltage.

The impedance measurement device 120 may obtain impedance spectrum data by measuring a plurality of impedances based on changing frequencies of the input current within a predetermined frequency range (e.g., a frequency range of 1 kilohertz (kHz) to hundreds of megahertz (MHz)).

The impedance measurement device 120 may use a battery, embedded in a main housing of the apparatus 1 for analyzing an in vivo component, as a current source. Alternatively, when the impedance measurement device 120 is connected via a wired or wireless connection to an external device to receive power from the external device, the impedance measurement device 120 may use a power source of the external device.

Referring to FIG. 2A, in an example embodiment, the impedance sensor 110 may include a channel formed in a main body substrate 20a configured to store a fluid, and the impedance sensor 110 may measure impedance in vitro while the fluid to be analyzed flows in the channel. As illustrated in FIG. 2A, the channel may include an inlet FCi, through which the fluid is introduced, a storage FCr, in which the introduced fluid is stored, and an outlet FCo, through which the fluid is discharged. The first electrode 21a may be disposed to contact a first side of the storage FCr of the channel, and the second electrode 21b may be disposed to contact a second side of the storage FCr of the channel. In this case, the fluid to be analyzed may be blood obtained invasively from an object, or may be a sample solution which includes similar physical properties as blood.

Referring to FIG. 2B, in an example embodiment, the impedance sensor 110 may measure impedance of in vivo blood. In this case, the fluid channel FC of the fluid to be analyzed may be a blood vessel portion of an object. FIG. 2B illustrates an example in which the channel is a blood vessel portion in the back of the hand, but is not limited thereto, and may be any object portion of the whole body, from which bio-impedance may be measured. A first electrode 22a and a second electrode 22b of the impedance sensor 110 may include various shapes on the substrate 20b, and may measure impedance from the blood vessel of the object. For example, as illustrated in FIG. 2B, the first electrode 22a and the second electrode 22b may be disposed to face each other with a distance therebetween, and a blood vessel portion may be positioned between the first electrode 22a and the second electrode 22b. The arrangement of the first electrode 22a and the second electrode 22b is not limited, and the first electrode 22a and the second electrode 22b may include various shapes based on an object portion, user characteristics, types of in vivo components, and the like.

The processor 200 may control various operations of the apparatus 1 for analyzing an in vivo component. For example, based on a user input or an occurrence of an event of in vivo component analysis at predetermined intervals, the processor 200 may control the impedance measurement device 120. The processor 200 may be connected to the impedance measurer 120, and may analyze an in vivo component by receiving impedance data measured by the impedance measurement device 120. In this case, the in vivo component may include blood glucose, cholesterol, triglyceride, protein, uric acid, and the like, but is not limited thereto.

Hereinafter, an example of a processor 200 will be described with reference to FIGS. 3 to 4B.

Figure 3:
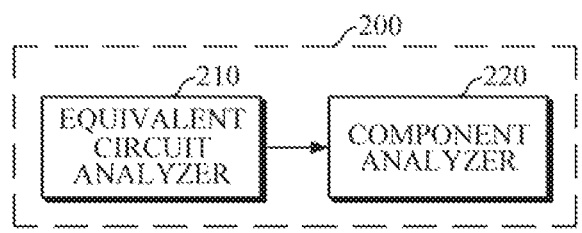
FIG. 3 is a block diagram illustrating a processor of an apparatus for analyzing an in vivo component according to an example embodiment.
Figure 4A:
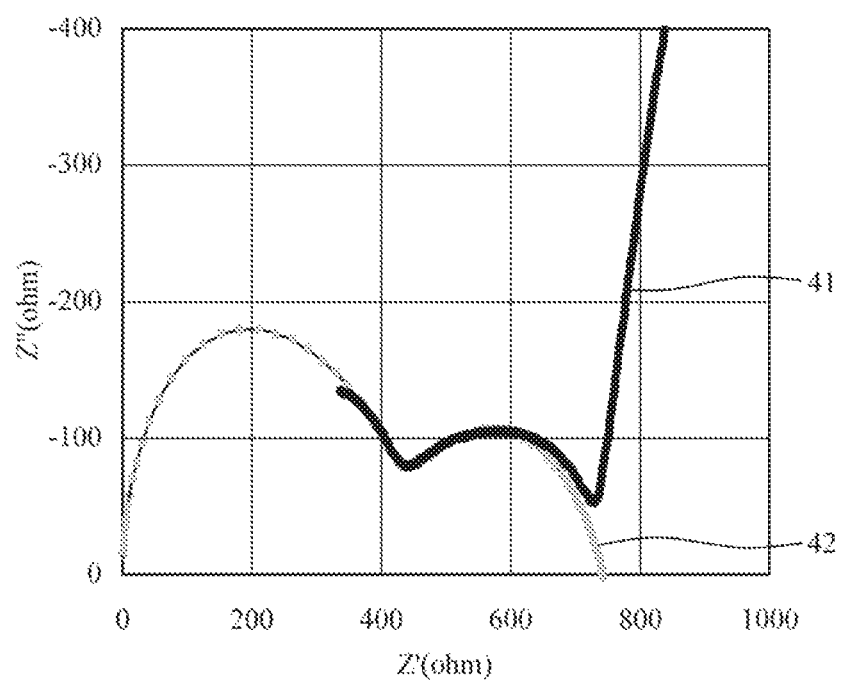
FIGS. 4A and 4B are diagrams explaining equivalent circuit modeling according to an example embodiment.

FIG. 3 is a block diagram illustrating an example of a processor of an apparatus for analyzing an in vivo component according to an example embodiment. FIGS. 4A and 4B are diagrams explaining equivalent circuit modeling according to an example embodiment.

Referring to FIG. 3, the processor 200 includes an equivalent circuit analyzer 210 and a component analyzer 220.

The equivalent circuit analyzer 210 may extract parameters related to the physical properties of the fluid to be analyzed by modeling the measured impedance using an equivalent circuit. In this case, the equivalent circuit may include a plurality of resistors and a plurality of capacitors. In this case, at least some of the capacitors may include a constant phase element (CPE), which is an element having properties between the resistor and the capacitor, and may be represented by the following Equation 1.

$$Z_{CPE} = \frac{1}{C(2\pi f j)^\alpha} \quad \text{[Equation 1]}$$

Referring to Equation 1, C denotes an amplitude of the CPE, f denotes a frequency, and a denotes a characteristic value between resistor and capacitor characteristics and may be, for example, a value between 0.5 to 1 in the case of human skin.

The equivalent circuit analyzer 210 may derive the effect of noise, such as a parasitic component or a polarization effect of the impedance sensor 110, by using a substance other than the fluid to be analyzed, for example, air, water, a reference solution, and the like. The equivalent circuit analyzer 210 may model an equivalent circuit of the impedance, measured by the impedance sensor 110, by reflecting the derived noise effect.

For example, the equivalent circuit analyzer 210 may estimate a parasitic component, and the like, of the impedance sensor 110 by using impedances measured in repetitive experiments based on air, water, a reference solution, or the like, which is introduced into the fluid channel FC instead of the fluid to be analyzed. In this case, the reference solution may include a conductive solution.

FIG. 4A illustrates raw impedance data 41, and pure blood impedance data 42, from which noise, such as a sensor parasitic component or a polarization effect, is eliminated from the raw impedance data. FIG. 4B illustrates an equivalent circuit 43 of the raw impedance data 41 measured by the impedance sensor 110, and an equivalent circuit 44 of the pure blood impedance data 42, from which noise such as a sensor parasitic component or a polarization effect is eliminated.

As illustrated in FIG. 4A, the raw impedance data 41, which is measured while based on changing frequencies, may include noise such as a parasitic component, a polarization effect, and the like, of the impedance sensor 110. Referring to FIG. 4B, by including a capacitor, which represents a parasitic component of the impedance sensor 110 which is previously measured using a substance other than the fluid to be analyzed (e.g., air, water, a reference solution, and the like) and a constant phase element (CPE)

which represents a polarization effect, the equivalent circuit analyzer 210 may model the raw impedance data 41 using the equivalent circuit 43.

Figure 4B:
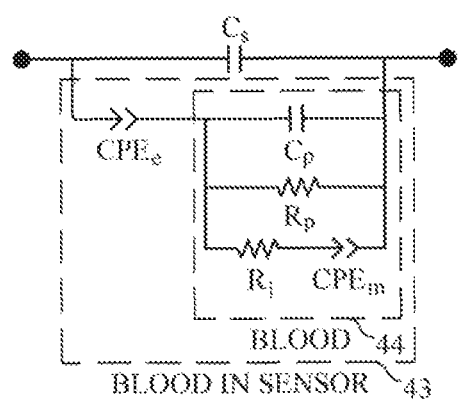

Referring to FIG. 4B, the equivalent circuit analyzer 210 extract parameters related to the physical properties of the fluid to be analyzed by using the modeled equivalent circuit 43. For example, the equivalent circuit analyzer 210 may obtain parameters, related to the physical properties of the fluid, from elements constituting a circuit 44 of the remaining blood, which is obtained by eliminating the already known parasitic capacitance (Cs) and the polarization effect (CPEe) from the modeled equivalent circuit 43. For example, the equivalent circuit analyzer 210 may extract, as parameters, plasma capacitance (Cp), plasma resistance (Rp), cytoplasm resistance (Ri), an amplitude of the CPE of a cell membrane (CPEm) (denoted by C in the above Equation 1), a characteristic value (denoted by a in the above Equation 1), and the like.

The component analyzer 220 may analyze an in vivo component based on the parameters extracted by the equivalent circuit analyzer 210. The component analyzer 220 may estimate blood glucose by using any one of the extracted parameters (e.g., plasma resistance (Rp)) as a principal component. However, the component analyzer 220 is not limited thereto, and may analyze the in vivo component using one or more of the extracted parameters.

Based on extracting the parameters, the component analyzer 220 may normalize the extracted parameters based on a parameter at a reference time, and may obtain a parameter variation compared to the parameter at the reference time. In this case, the reference time may include a time of fasting (e.g., a fasting interval), and may be a calibration time. For example, the component analyzer 220 may normalize the parameters by subtracting the parameter value at the reference time from the measured parameter value, and by dividing the subtracted value by the parameter at the reference time.

Based on calculating the parameter variation, the component analyzer 220 may obtain an estimated in vivo component value by applying a pre-defined in vivo component analysis model to the parameter variation.

For example, the in vivo component analysis model may be an analysis model which defines a relationship between the normalized plasma resistance parameter (Rp) and blood glucose. The in vivo component analysis model may be a linear function as illustrated herein, but is not limited thereto, and may be defined by various other methods such as linear/nonlinear regression analysis, a neural network, deep learning, and the like.

Figure 5:
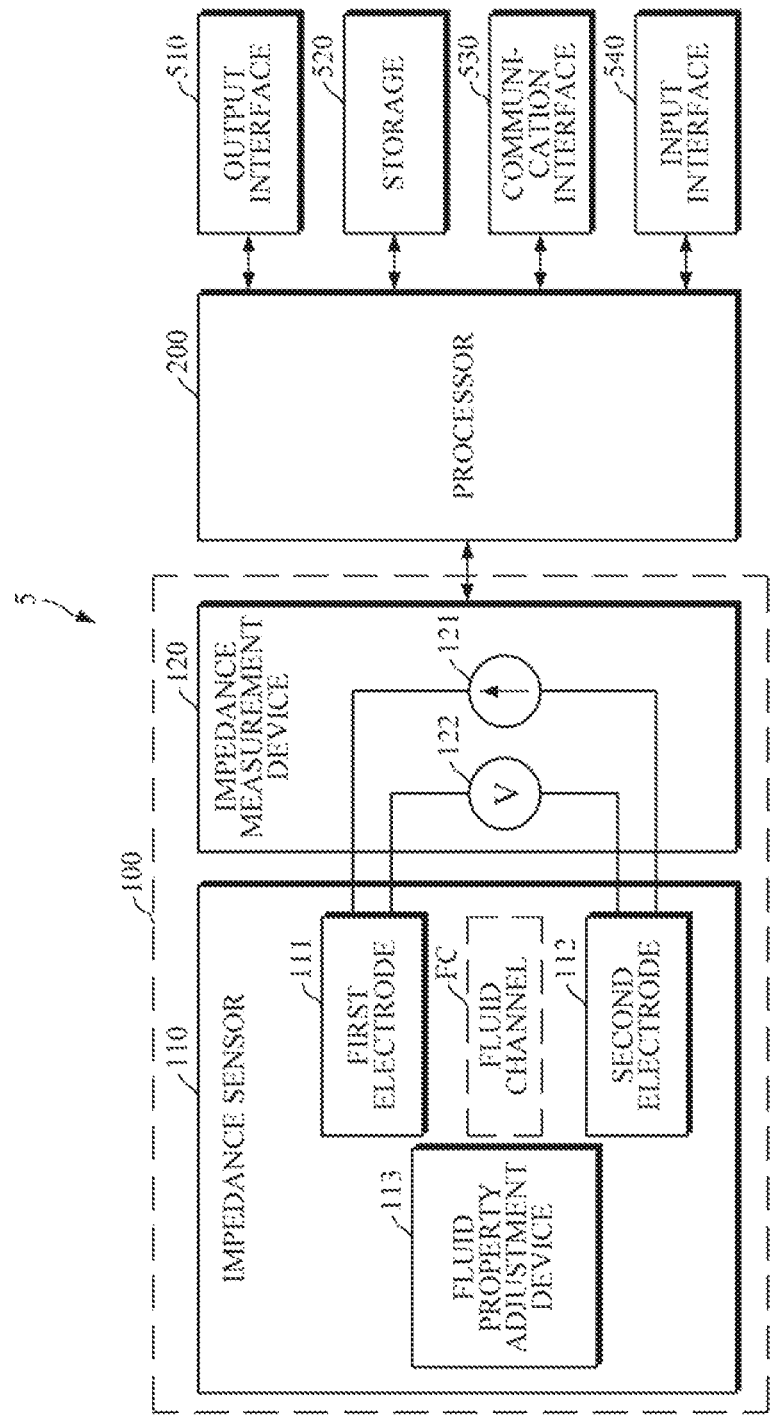
FIG. 5 is a block diagram illustrating an apparatus for analyzing an in vivo component according to an example embodiment.

FIG. 5 is a block diagram illustrating an apparatus for analyzing an in vivo component according to an example embodiment.

Referring to FIG. 5, the apparatus 5 for analyzing an in vivo component includes an impedance sensor 110, an impedance measurement device 120, a processor 200, an output interface 510, a storage 520, a communication interface 530, and an input interface 540. The impedance sensor 110, the impedance measurer 120, and the processor 200 may be substantially the same as the impedance sensor 110, the impedance measurer 120, and the processor 200 of FIGS. 1 to 4B, such that detailed description thereof will be omitted.

The output interface 510 may provide a processing result of the processor 200 to a user. For example, the output interface 510 may visually output the processing result via a display module and the like. The output interface 510 may divide a display area into two or more areas, and may output information, such as impedance information used for analyzing an in vivo component, in a first area of the display. Along with the information, the output interface 510 may output an analysis result of an in vivo component, such as an estimated in vivo component value in a second area of the display. Further, the output interface 510 may also output in vivo component analysis history data in the form of graphs. Based on a user input that selects an analysis result of an in vivo component at a particular time in a graph, the output interface 510 may output the information used for analyzing the in vivo component at the particular time and/or other detailed additional information in the first area of the display. In this case, if an estimated in vivo component value is outside of a normal range, the output interface 510 may provide the user with information, indicating that the estimated value is abnormal, by highlighting an abnormal value in red, and the like, or by displaying the abnormal value along with a normal range.

In another example, the output interface 510 may output an analysis result of an in vivo component in a non-visual manner by voice, vibrations, tactile sensation, and the like, using an audio output component (e.g., a speaker) or a haptic module, either alone or in combination with a visual display of an analysis result.

The storage 520 may store reference information for analyzing an in vivo component, an impedance measurement result, an analysis result of an in vivo component, and the like. In this case, the reference information may include user characteristic information such as a user's age, sex, health condition, and the like, as well as a parameter value at a reference time, an in vivo component analysis model, and the like.

The storage 520 may include at least one storage medium of a flash memory-type memory, a hard disk-type memory, a multimedia card micro-type memory, a card-type memory (e.g., a secure digital (SD) memory, an extreme digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communication interface 530 may communicate with an external device to transmit and receive various data related to analysis of an in vivo component. The external device may include an information processing device such as a smartphone, a tablet PC, a desktop computer, a laptop computer, and the like.

The communication interface 530 may communicate with the external device by using various wired or wireless communication techniques such as Bluetooth communication, Bluetooth Low Energy (BLE) communication, Near Field Communication (NFC), wireless local area network (WLAN) communication, Zigbee communication, Infrared Data Association (IrDA) communication, wireless fidelity (Wi-Fi) communication, Ultra-Wideband (UWB) communication, Ant+ communication, Wi-Fi Direct (WFD) communication, Radio Frequency Identification (RFID) communication, third generation (3G) communication, fourth generation (4G) communication, fifth generation (5G) communication, and the like. However, this is merely exemplary and is not intended to be limiting.

The input interface 540 may include a component that permits the apparatus 5 to receive information, such as via user input (e.g., a touch screen display, a keyboard, a keypad, a mouse, a button, a switch, and/or a microphone). Additionally, or alternatively, input interface 540 may include a sensor for sensing information (e.g., a global positioning system (GPS) component, an accelerometer, a gyroscope, and/or an actuator).

Figure 6:
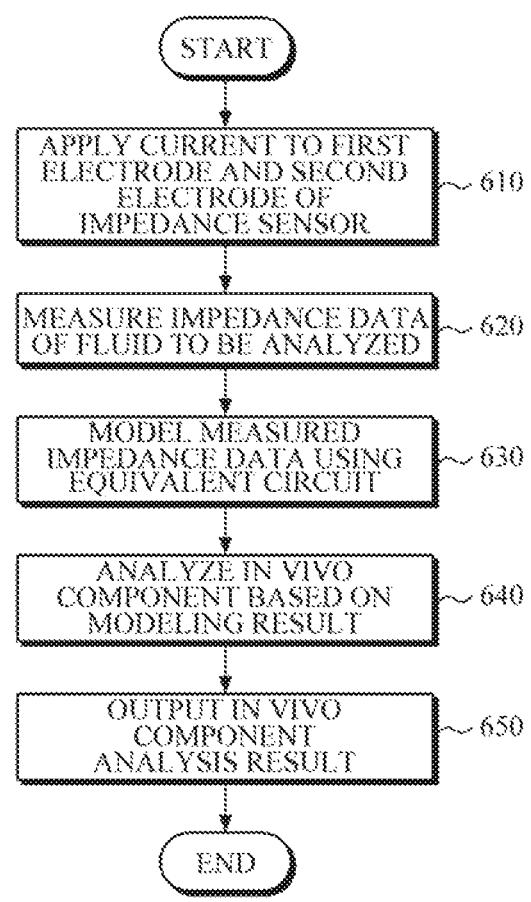
FIG. 6 is a flowchart illustrating a method of analyzing an in vivo component according to an example embodiment.

FIG. 6 is a flowchart illustrating a method of analyzing an in vivo component according to an example embodiment.

The method of analyzing an in vivo component of FIG. 6 may be performed by the apparatuses 1 and 5 for analyzing an in vivo component of FIGS. 1 and 5.

Referring to FIG. 6, the apparatuses 1 and 5 for analyzing an in vivo component may apply a current to the first electrode and the second electrode of the impedance sensor in operation 610. The first electrode and the second electrode may be configured to measure impedance using a two-electrode method, a four-electrode method, and the like. The first electrode and the second electrode may be disposed to face each other with a predetermined distance therebetween, and may contact a channel of a fluid to be analyzed.

The fluid to be analyzed may include blood, a fluid including similar properties as blood, and the like. The fluid channel may be a blood vessel portion of an object, or may be formed in the impedance sensor to store the fluid. In this case, the fluid channel may include an inlet, through which the fluid is introduced so that impedance may be measured by artificially flowing the fluid; a storage, in which the introduced fluid is stored; and an outlet, through which the fluid is discharged.

Properties such as temperature, flow, flow speed, and the like, of the fluid may be adjusted based on an in vivo component to be analyzed, performance of the apparatus, user characteristics, surrounding measurement environment, and the like. For example, in the case of measuring in vitro impedance of blood, temperature of the fluid in the channel may be adjusted to be similar to body temperature by using a thermostat. Further, the fluid in the channel may be adjusted to be similar to a normal flow and flow speed of blood in the human body, and the like by using a flow regulator and/or a flow speed regulator.

The apparatuses 1 and 5 for analyzing an in vivo component may measure impedance of the fluid to be analyzed in operation 620. For example, the apparatuses 1 and 5 for analyzing an in vivo component may measure the impedance of the fluid to be analyzed by measuring a voltage between both ends of the first electrode and the second electrode.

Subsequently, the apparatuses 1 and 5 for analyzing an in vivo component may model the measured impedance using an equivalent circuit in operation 630. The equivalent circuit may include a plurality of resistors and two or more capacitors. In this case, at least some of the capacitors may include a constant phase element (CPE) having properties between a resistor and capacitor.

For example, the apparatuses 1 and 5 for analyzing an in vivo component may model an equivalent circuit of blood in the impedance sensor. In this case, the apparatuses 1 and 5 for analyzing an in vivo component may derive the effect of noise, such as a parasitic component or a polarization effect, of the impedance sensor 110 by using a substance other than blood (e.g., air, water, a reference solution, and the like), and may model the equivalent circuit according to an entire sensor environment by including the derived parasitic component, polarization effect, and the like, in the equivalent circuit of pure blood.

Further, based on modeling the equivalent circuit, the apparatuses 1 and 5 for analyzing an in vivo component may extract one or more parameters from the equivalent circuit. For example, as the parasitic component parameter or the polarization effect parameter in the equivalent circuit of all the sensors is already known, the apparatuses 1 and 5 for analyzing an in vivo component may extract parameters, related to the physical properties of pure blood, from the rest of the equivalent circuit elements. For example, the parameters may include plasma capacitance, plasma resistance, cytoplasm resistance, and values indicative of an amplitude or a slope of the CPE of a cell membrane, and the like.

The apparatuses 1 and 5 for analyzing an in vivo component may analyze an in vivo component based on the modeling result in operation 640. The apparatuses 1 and 5 for analyzing an in vivo component may obtain an estimated in vivo component value, such as blood glucose, cholesterol, triglyceride, protein, uric acid, and the like, based on the parameters extracted in operation 630.

For example, the apparatuses 1 and 5 for analyzing an in vivo component may obtain a variation in the parameters extracted from the equivalent circuit compared to a reference time, and may obtain the estimated in vivo component value by using the in vivo component analysis model which defines a relationship between the obtained variation and an in vivo component. For example, upon extracting plasma resistance as a principal component, the apparatuses 1 and 5 for analyzing an in vivo component may obtain a variation in plasma resistance compared to a reference time, and may obtain an estimated blood glucose value by inputting the obtained variation in plasma resistance to a blood glucose analysis model.

Next, the apparatuses 1 and 5 for analyzing an in vivo component may output an in vivo component analysis result in operation 650. The apparatuses 1 and 5 for analyzing an in vivo component may output the in vivo component analysis result in a visual and/or non-visual manner using various output devices such as a display, a speaker, a haptic device, and the like.

Figure 7:
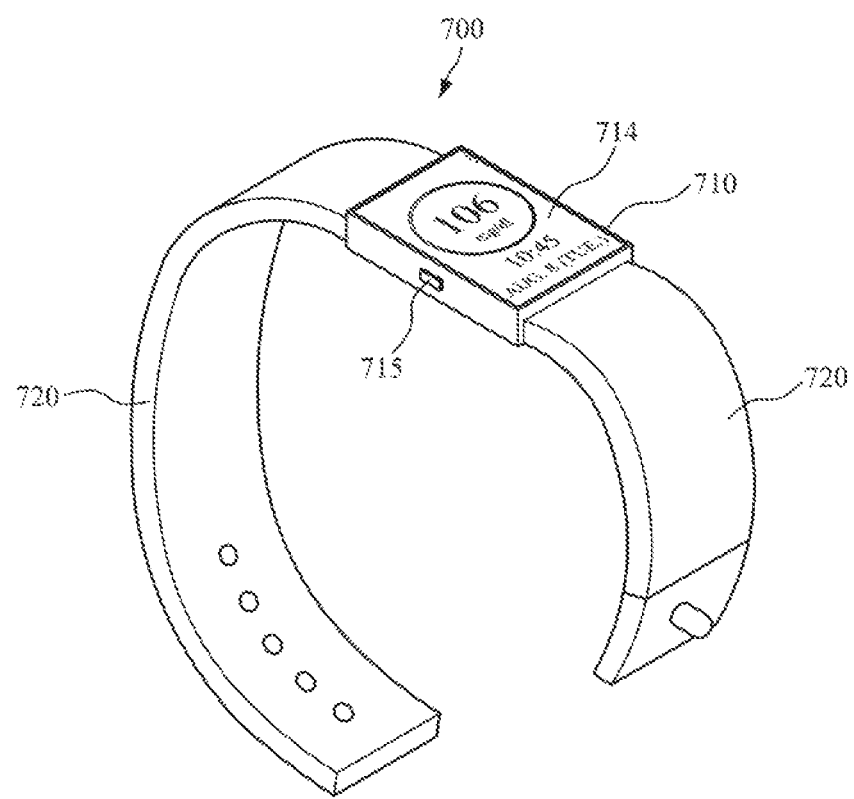
FIG. 7 is a diagram illustrating a wearable device according to an example embodiment.

FIG. 7 is a diagram illustrating a wearable device according to an example embodiment. FIG. 7 illustrates a wearable device such as a smart watch or a smart band which is worn on a user's wrist, and in which the apparatuses 1 and 5 for analyzing an in vivo component of FIGS. 1 and 5 may be disposed.

Referring to FIG. 7, the wearable device 700 includes a main body 710 and a strap 720. Various components of the apparatuses 1 and 5 for analyzing an in vivo component may be embedded in the main body 710.

The main body 710 may be worn on a user's wrist via the strap 720, and the strap 720 may be connected to both sides of the main body 710 so that both ends of the strap 720 may be fastened to each other. The strap 720 may be made of a flexible material to allow the main body 710 to be wrapped around a user's wrist.

A battery, which supplies power to the wearable device 700, may be embedded in the main body 710 or the strap 720.

The main body 710 may include an impedance sensor which obtains an impedance spectrum from the user's wrist. The impedance sensor may include a plurality of electrodes, which may be spaced apart from each other so that each of the electrodes may measure impedance of blood while being in contact with both sides of the blood vessel. However, the measurement of impedance is not limited to the blood vessel, and may include any body part, such as the back of the hand, the wrist, fingers, the upper body, the face, and the like, where bio-impedance may be measured.

The main body 710 may include a camera, which may obtain an image of an object based on the object contacting the main body 710.

A processor may be mounted in the main body 710, may be connected to various components, may control the various components, and may process information collected therefrom. For example, based on receiving an image of the object from the camera, the processor may provide, for output, information that guides a contact position, a contact state, and the like, for a user.

The processor may analyze an in vivo component by using an impedance measurement result. The processor may extract parameters related to the physical properties of blood by modeling the measured impedance using an equivalent circuit, and may estimate blood glucose by using a variation in the extracted parameters. The equivalent circuit may include a plurality of resistors and capacitors, in which case some of the capacitors may include a CPE. Further, by excluding previously obtained parameters of noise elements from the modeled equivalent circuit, the processor may extract parameters from the rest of the elements.

The processor may output the in vivo component analysis result to a user via a display 714.

The display 714 may be mounted at the top of the main body 710, and may output a variety of information under the control of the processor. Further, the display 714 may include a touch screen as an input interface which allows touch input, and may receive a touch input from a user and transmit the received input to the processor.

A communication interface may be mounted in the main body 710, and may communicate with an external device. The communication interface may transmit the in vivo component analysis result to the external device, so that the external device may perform various functions related to monitoring of a user's health condition. The external device may be an information processing device, such as a smartphone, a tablet PC, a desktop computer, a laptop computer, and the like, which has relatively high computing performance.

The wearable device 700 may further include an input interface 715. The input interface 715 may be mounted on one side of the main body 710 so as to be exposed to the outside, and may receive an instruction input by a user and transmit the received instruction to the processor. The input interface 715 may include a function to power on/off the wearable device 700.

The present disclosure can be implemented by computer-readable code stored on a non-transitory computer-readable medium. The computer-readable medium may be any type of recording device in which data is stored in a computer-readable manner.

Examples of the computer-readable medium include a ROM, a RAM, a CD-ROM, a magnetic tape, a floppy disc, an optical data storage, and a carrier wave (e.g., data transmission through the Internet). The computer-readable medium can be distributed via a plurality of computer systems connected via a network so that computer-readable code is written thereto and executed therefrom in a decentralized manner. Functional programs, code, and code segments for implementing the present disclosure can be readily deduced by programmers in the technical field to which the disclosure pertains.

The present disclosure has been described herein with regard to example embodiments. However, it will be obvious to those skilled in the art that various changes and modifications can be made without changing technical ideas and essential features of the present disclosure. Thus, it is clear that the above-described example embodiments are illustrative in all aspects and are not intended to limit the present disclosure.

What is claimed is:

1. An apparatus for analyzing an in vivo component, the apparatus comprising:
    an impedance sensor comprising a first electrode configured to contact a first side of a fluid channel of a fluid to be analyzed, and a second electrode configured to contact a second side of the fluid channel, wherein the first side and the second side of the fluid channel oppose each other;
    an impedance measurement device configured to:
        apply a current to the first electrode and the second electrode;
        measure a voltage between the first electrode and the second electrode based on applying the current; and
        measure an impedance of the fluid based on the measured voltage while the fluid is flowing through the fluid channel disposed between the first electrode and the second electrode, during a state in which the impedance sensor is in contact with an object;
    a memory configured to store a parameter at a reference time; and
    a processor configured to:
        model an equivalent circuit equivalent to the impedance measured at an estimation time after the reference time; and
        analyze the in vivo component based on the modeled equivalent circuit,
    wherein the processor is further configured to:
        extract one or more parameters, related to properties of the fluid to be analyzed, based on the modeled equivalent circuit;
        obtain a parameter variation by normalizing the extracted one or more parameters using the parameter at the reference time stored in the memory;
        obtain an in vivo component value, including at least one of blood glucose, cholesterol, triglyceride, protein, and uric acid, by applying an in vivo component estimation model to the parameter variation, and
    wherein the one or more parameters comprise at least one of plasma resistance, cytoplasm resistance, plasma capacitance, and constant phase element (CPE) of a cell membrane.

2. The apparatus of claim 1, wherein the impedance measurement device is further configured to measure the impedance at a plurality of frequencies within a predetermined range.

3. The apparatus of claim 1, wherein the equivalent circuit comprises a plurality of resistors and a plurality of capacitors.

4. The apparatus of claim 1, wherein the processor is further configured to reduce an effect of noise, including at least one of a parasitic component and a polarization effect of the impedance sensor, from the measured impedance.

5. The apparatus of claim 1, wherein the reference time corresponds to a fasting interval.

6. The apparatus of claim 1, wherein the fluid channel of the fluid to be analyzed comprises a blood vessel portion of the object.

7. The apparatus of claim 1, wherein the fluid channel of the fluid to be analyzed comprises:
    an inlet configured to introduce the fluid to be analyzed;
    a storage configured to store the fluid introduced via the inlet; and
    an outlet configured to discharge the fluid stored in the storage.

8. The apparatus of claim 1, wherein the impedance sensor is further configured to adjust a temperature of the fluid based on a temperature of the object, and wherein the impedance measurement device is further configured to measure the impedance of the fluid based on the measured voltage while the fluid having the adjusted temperature is flowing through the fluid channel disposed between the first electrode and the second electrode, during the state in which the impedance sensor is in contact with the object.

9. The apparatus of claim 1, wherein the first electrode and the second electrode are disposed to face each other.

* * * * *